US012714793B2

United States Patent
(12) United States Patent
McCawley et al.

(10) Patent No.: US 12,714,793 B2
(45) Date of Patent: Aug. 25, 2026

(54) GAS POWERED AUTO-INJECTORS AND METHODS FOR USE

(71) Applicant: ALTAVIZ, LLC, Irvine, CA (US)

(72) Inventors: Matthew McCawley, San Clemente, CA (US); Jack R. Auld, Laguna Niguel, CA (US)

(73) Assignee: ALTAVIZ, LLC, Irvine, CA (US)

( * ) Notice: Subject to any disclaimer, the term of this patent is extended or adjusted under 35 U.S.C. 154(b) by 825 days.

(21) Appl. No.: 18/076,335

(22) Filed: Dec. 6, 2022

(65) Prior Publication Data

US 2023/0173184 A1 Jun. 8, 2023

Related U.S. Application Data

(60) Provisional application No. 63/286,508, filed on Dec. 6, 2021.

(51) Int. Cl.
*A61M 5/20* (2006.01)
*A61M 5/32* (2006.01)

(52) U.S. Cl.
CPC .......... *A61M 5/2046* (2013.01); *A61M 5/322* (2013.01); *A61M 2005/208* (2013.01)

(58) Field of Classification Search
CPC ................ A61M 5/2046; A61M 5/322; A61M 2005/208; A61M 5/3243; A61M 5/3234; A61M 2005/2013; A61M 2005/206; A61M 5/2033; A61M 5/2053
See application file for complete search history.

(56) References Cited

U.S. PATENT DOCUMENTS

| | | | | |
|---|---|---|---|---|
| 2013/0317478 A1* | 11/2013 | Auld | ..................... | A61M 5/482 604/118 |
| 2014/0330204 A1 | 11/2014 | Huculak et al. | | |
| 2019/0167906 A1* | 6/2019 | Auld | ..................... | A61M 5/322 |

OTHER PUBLICATIONS

Korean Intellectual Property Office, International Search Report for corresponding International Application No. PCT/US2022/052050, Apr. 17, 2023, 5 pages.
Korean Intellectual Property Office, Written Opinion for corresponding International Application No. PCT/US2022/052050, Apr. 17, 2023, 6 pages.

* cited by examiner

*Primary Examiner* — Wesley G Harris
*Assistant Examiner* — Neeraja Gollamudi
(74) *Attorney, Agent, or Firm* — William A. English; Vista IP Law Group LLP

(57) ABSTRACT

An auto-injector includes a drive assembly within a housing carrying a syringe including a needle adjacent an activation cap within the housing's distal end. The drive assembly includes a first chamber carrying a gas canister, a plunger within a second chamber coupled to the syringe, and proximal and distal chambers. The activation cap is pressed against a subject's skin to direct the drive assembly proximally to open an outlet of the canister to release pressurized gas into the first chamber, whereupon the gas enters the proximal chamber to generate a distal force to advance the drive assembly to direct the needle into the subject and enters the second chamber to advance the plunger to deliver agents from the syringe into the subject. After the plunger advances, the gas enters the distal chamber to generate a proximal force to retract the drive assembly to direct the needle back into the housing.

21 Claims, 8 Drawing Sheets

A
18
8a
8c
60
20
40
8
24
50
6
76
74
70
72
8b
72a
80
78
86
A
18

18
8c
8d
14a
32a
60
8a
22c
28
30
9a
10a
22b
32b
40
22a
42
20
42a
22
50
24
50
98b
6
96
56
26
10b
90
94
98a
54
16
76
75
72b
74
70
9b
72
72
72a
8b
78
80
86
18

64a
60
8a
40
20
22
24
26
12
52
53
50
6
8
54
74
70
73
83
82
8b
78
80
84

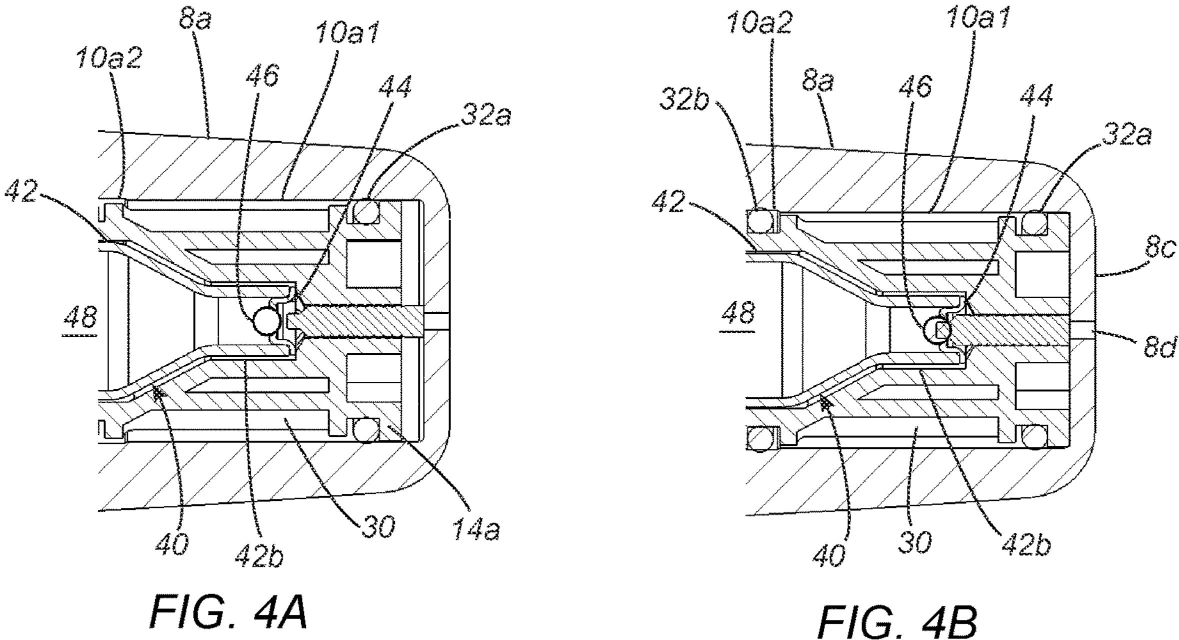
FIG. 4A
FIG. 4B
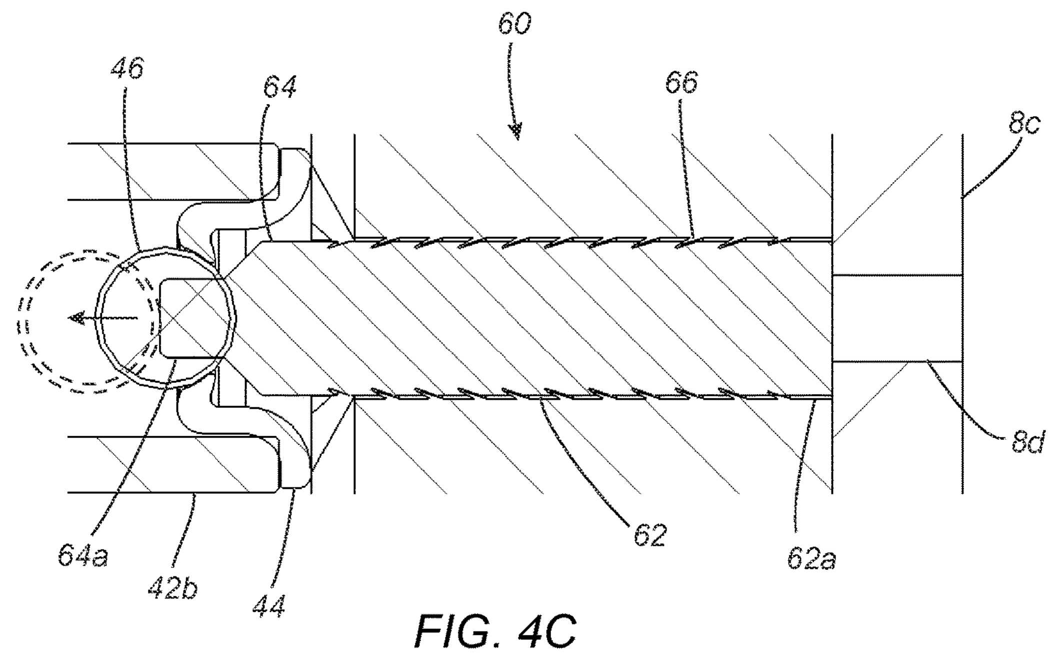
FIG. 4C 8a
60
40
8
6
26
98b
96
53
92
94
98a
52c
90
50
56
70
54
75
74
8b
80
78

10b2
GAS
10b1
52a

GAS POWERED AUTO-INJECTORS AND METHODS FOR USE

RELATED APPLICATION DATA

The present application claims benefit of U.S. provisional application Ser. No. 63/286,508, filed Dec. 6, 2021, the entire disclosure of which is expressly incorporated by reference herein.

TECHNICAL FIELD

The present application relates generally to devices and methods for delivering agents into a subject's body and, more particularly, to auto-injectors and/or gas-powered drive systems for injection devices, and to methods for making and using such devices.

BACKGROUND

There are many applications involving delivery of a medicament or other agent subcutaneously, intramuscularly, or otherwise into a patient's body. For example, auto-injectors are available that include a predetermined dose of the agent that may be delivered automatically into the patient's body, e.g., after placement against the patient's skin and activation. Generally, such auto-injectors are spring-loaded syringes that are activated to release the spring, which generates sufficient force to penetrate the skin with a needle and deliver the dose within the syringe. For viscous fluids, the forces required to develop fluid flow can be higher than spring-powered systems can provide. When springs can be used, they must generate a relatively high force that requires springs of high mass. Consequently, such auto-injectors may make substantial noise, create pressure spikes in the syringe leading to glass breakage, vibrate, and/or may drive the needle forcefully into the patient's skin, which may cause pain and/or may startle the user, particularly when the patient is administering the injection themselves.

Therefore, improved devices and methods for delivering agents into a patient's body would be useful.

SUMMARY

The present application relates generally to devices and methods for delivering agents into a subject's body and, more particularly, to auto-injectors and/or gas-powered drive systems for injection devices, and to methods for making and using such devices.

In accordance with one example, a device is provided for delivering one or more agents into a subject's body that includes an outer housing comprising a proximal end and a distal end; an activation cap mounted on the distal end of the housing such that a contact surface is disposed distal to the distal end of the housing; a drive assembly slidable within the housing; a syringe on a distal end of the drive assembly such that a needle of the syringe is disposed adjacent the activation cap within the distal end of the housing; a gas canister within a first chamber within a proximal end of the drive assembly; a plunger comprising a proximal end within a second chamber of the drive assembly and a distal end coupled to a piston of the syringe; and an opener pin adjacent an outlet of the gas canister; the activation cap movable related to the housing such that, when the contact surface of the activation cap is pressed against a subject's skin, the activation cap is configured to move proximally to direct the drive assembly proximally within the housing to cause the opener pin to open the outlet of the gas canister to release pressurized gas into the first chamber; and the drive assembly comprising a pair of proximal seals sealing a proximal chamber communicating with the first chamber, the proximal seals configured such that, when the pressurized gas is released, the pressurized gas generates a distal force to advance the drive assembly distally to direct the needle out the distal end of the housing into the subject's skin and the pressurized gas enters the second chamber to direct the plunger distally from an initial position towards a final position to deliver the one or more agents from the syringe through the needle into the subject. Optionally, the drive assembly may also include a pair of distal seals sealing a distal chamber and a passage that communicates with the second chamber when the plunger reaches the final position, the distal seals configured such that, when the pressurized gas enters the distal chamber, the pressurized gas generates a proximal force to retract the drive assembly proximally to direct the needle back into the distal end of the housing.

In another example, a device is provided for delivering one or more agents into a subject's body that includes an outer housing comprising a proximal end and a distal end; an activation cap mounted on the distal end of the housing such that a contact surface is disposed distal to the distal end of the housing; a drive assembly slidable within the housing; a syringe on a distal end of the drive assembly such that a needle of the syringe is disposed adjacent the activation cap within the distal end of the housing; a gas canister within a first chamber within a proximal end of the drive assembly; a plunger comprising a proximal end within a second chamber of the drive assembly and a distal end coupled to a piston of the syringe; and an opener pin adjacent an outlet of the gas canister; the activation cap movable related to the housing such that, when the contact surface of the activation cap is pressed against a subject's skin, the activation cap is configured to move proximally to direct the drive assembly proximally within the housing to cause the opener pin to open the outlet of the gas canister to release pressurized gas into the first chamber; and the drive assembly comprising a pair of distal seals sealing a distal chamber and a passage that communicates with the second chamber when the plunger reaches the final position, the distal seals configured such that, when the pressurized gas enters the distal chamber, the pressurized gas generates a proximal force to retract the drive assembly proximally to direct the needle back into the distal end of the housing.

In accordance with still another example, a method is provided for delivering one or more agents into a subject's body that includes providing an injection device comprising an outer housing comprising a proximal end and a distal end; an activation cap mounted on the distal end of the housing such that a contact surface is disposed distal to the distal end of the housing; a drive assembly slidable within the housing; a syringe on a distal end of the drive assembly such that a needle of the syringe is disposed adjacent the activation cap within the distal end of the housing; a gas canister within a first chamber within a proximal end of the drive assembly; a plunger comprising a proximal end within a second chamber of the drive assembly and a distal end coupled to a piston of the syringe; and an opener pin adjacent an outlet of the gas canister; placing the contact surface against the subject's skin; and pressing the device to cause the activation cap to move proximally to direct the drive assembly proximally within the housing to cause the opener pin to open the outlet of the gas canister to release pressurized gas into the first chamber, whereupon the pressurized gas enters a proximal chamber of the drive assembly sealed by a pair of proximal seals configured such that the pressurized gas generates a distal force to advance the drive assembly distally to direct the needle out the distal end of the housing into the subject's skin; the pressurized gas enters the second chamber to direct the plunger distally from an initial position towards a final position to deliver the one or more agents from the syringe through the needle into the subject. Optionally, when the plunger reaches the final position, the pressurized gas enters a distal chamber sealed by a pair of distal seals such that the pressurized gas generates a proximal force to retract the drive assembly proximally to direct the needle back into the distal end of the housing.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

FIGS. 4A and 4B are details showing an opener pin opening a gas canister to release pressurized gas to power the device.

FIG. 4C is a detail showing an example of an opener pin that includes features to prevent reclosure of the gas canister once opened.

DETAILED DESCRIPTION

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Figures 1A, 1B:
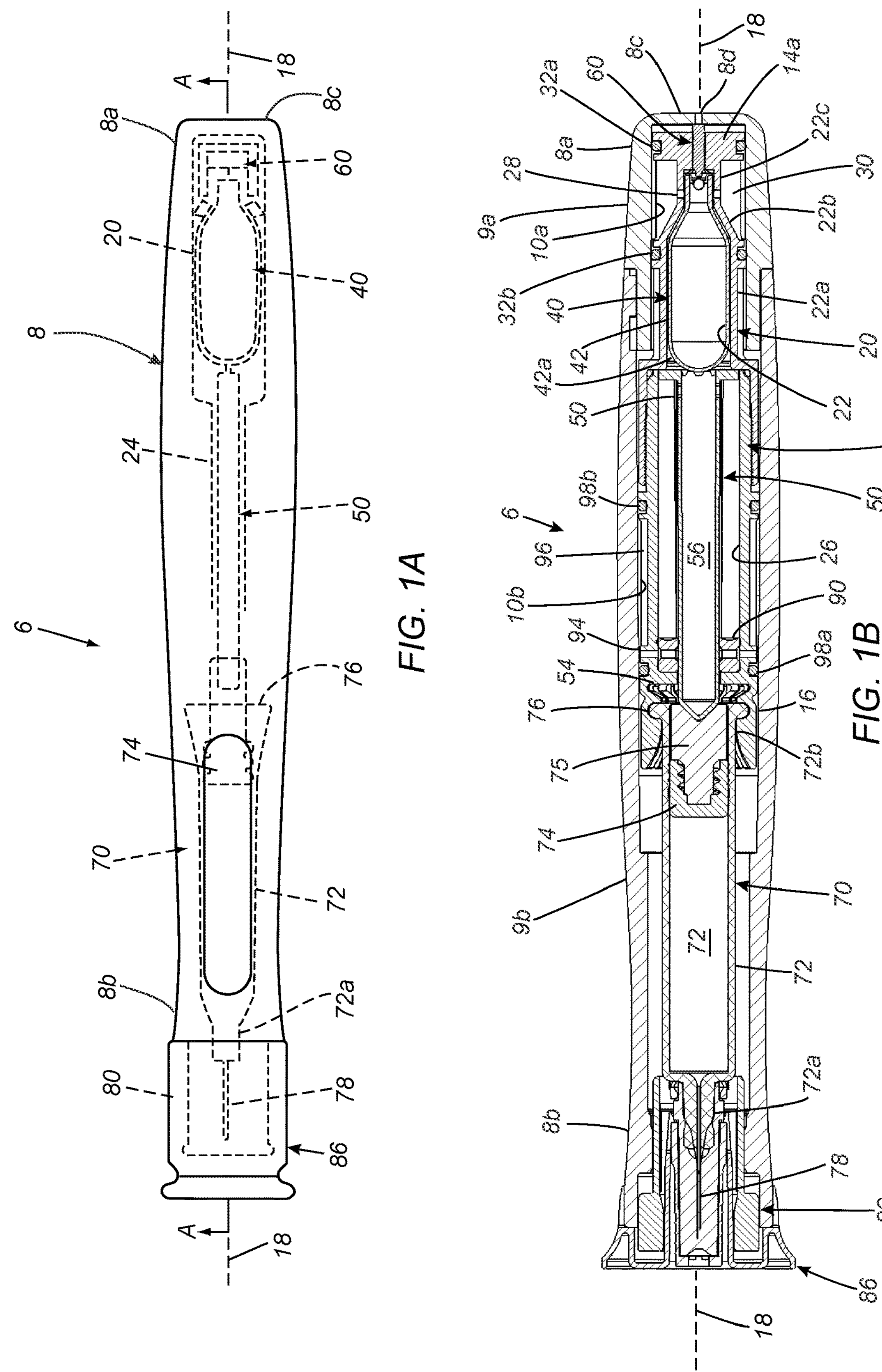
FIGS. 1A and 1B are side and cross-sectional views of an exemplary auto-injector device including a drive assembly coupled to a syringe within an outer housing.

Turning to the drawings, FIGS. 1A and 1B show an example of an auto-injector device 6 that includes an outer housing 8, a drive assembly 12 movably received within the housing 8 that includes a gas canister or other source of pressurized gas 40 to power the device 6, a syringe 70 including a needle 78 for delivering one or more agents into a subject's body, and a plunger 50. The device 6 also includes an activation cap 80 and an opener mechanism 60 for opening the canister 40 to release pressurized gas within the canister 40 into a set of chambers of the device 6. Generally, the drive assembly 12 is configured such that, upon activation by the activation cap 80, the pressurized gas is released from the canister 40 into the chambers of the device 6 to generate a distal force to advance the drive assembly 12 to direct the needle 78 into the subject's skin, to advance the plunger 50 to deliver the agent(s) from the syringe 70 into the subject and, after the plunger 50 advances, to generate a proximal force to retract the drive assembly 12 to direct the needle 78 back into the housing 8. Thus, once the activation cap 80 activates the device 6, the entire operation is powered automatically by the release of the pressurized gas without further action by the operator. As used herein, "agent" may include one or more therapeutic and/or diagnostic compounds or materials, e.g., in liquid or gaseous form, in solution or suspension, and the like, such as viscous fluids.

Generally, the outer housing 8 includes a proximal end 8*a*, a distal end 8*b*, and an inner wall 10*a*, 10*b* extending therebetween. The outer surface between the proximal and distal ends 8*a*, 8*b* may be sized and/or shaped to facilitate manipulation of the device 6, e.g., to facilitate placing and pressing the activation cap 80 against a subject's skin to activate the device 6 and inject the agent(s). For example, the outer surface may have a generally cylindrical shape optionally including one or more textures or grip features to facilitate an operator holding the device 6 in one hand and pressing the activation cap 80 against their skin, as described further elsewhere herein. As shown, the proximal end 8*a* of the housing 8 may include a wall 8*c* enclosing the proximal end 8*a* that includes a vent 8*d* to allow air to enter and/or exit the housing 8 as needed to avoid interference with movement of the drive assembly 12.

The housing 8 may be formed from multiple, separate components, e.g., clamshell halves, e.g., formed from metal, such as steel, aluminum, and the like, plastic, and/or composite material, by one or more of cold drawing, molding, casting, machining, and the like, that are substantially permanently attached together, e.g., by one or more of welding, soldering, fusing, bonding with adhesive, interference fit, and the like. Alternatively, the housing 8 may be formed as a single, integral component. For example, as shown, the housing 8 may include a first portion 9*a* including the proximal end 8*a* that includes an inner wall 10*a*, and a second portion 9*b* permanently attached to the first portion 9*a* including the distal end 8*b* that includes an inner wall 10*b* that has a larger cross-section than the inner wall 10*a*. As described further elsewhere herein, each inner wall 10*a*, 10*b* may have multiple regions having different substantially uniform inner diameters or other cross-sections, which cooperate with seals of the drive assembly 12 to generate the forces necessary to direct the drive assembly 12 distally and proximally during operation of the device 6.

The drive assembly 12 includes a proximal end 14 and a distal end 16 aligned along a longitudinal axis 18, e.g., such that the drive assembly 12 may move distally and proximally along the axis 18 within the housing 8 during operation of the device 6, as described elsewhere herein. The drive assembly 12 may be formed as a single, integral component, e.g., from metal, such as steel, aluminum, and the like, plastic, and/or composite material, by one or more of cold drawing, molding, casting, machining, and the like. Alternatively, the drive assembly 12 may be formed from multiple, separate components that are substantially permanently attached together, e.g., by one or more of welding, soldering, fusing, bonding with adhesive, interference fit, and the like.

In the example shown in FIG. 1B, the drive assembly 12 may be formed as a first or proximal portion 20 adjacent the proximal end 14 defining a first chamber 22 for receiving the canister 40, and a separate second or distal portion 24 adjacent the distal end 16 defining a second chamber 26 communicating with the first chamber 22 that receives the plunger 50. Both housing portions 20, 24 may have a generally cylindrical or other appropriate shape, e.g., defining one or more additional chambers or regions that are spaced apart along the length of the drive assembly 12, as described further below. The proximal and distal portions 20, 24 may be permanently connected together, e.g., by one or more of mating threads 25, force fit, bonding with adhesive, sonic welding, fusing, and the like.

For example, the proximal portion 20 may include an annular wall surrounding the first chamber 22 that includes a uniform diameter first region 22*a*, a tapered region 22*b*, and a uniform diameter second region 22*c* sized to receive the canister 40 while allowing pressurized gas released from the canister 40 to pass distally around the canister 40 into the second chamber 24. In addition, the proximal portion 20 includes one or more passages 28 extending through the annular wall, e.g., a pair of passages 28 extending through the second region 22*c* into a proximal chamber 30 surrounding a portion of the proximal portion 20, e.g., between the annular wall regions 22*b*, 22*c* and the inner wall 10*a* of the housing 8. The drive assembly 12 may include a proximal hub 14*a* proximal to the first chamber 20, e.g., coupled to the annular wall such that the hub 14*a* extends outwardly to the inner wall 10*a* of the housing 8.

Generally, with additional reference to FIGS. 4A-4C, the canister 40 includes a body 42 including a first closed end 42*a*, a second outlet end 42*b*, and a cap 44 with a closure 46 welded or otherwise attached to the outlet end 42*b* to provide an enclosed cavity 48 filled with a fluid containing liquefied gas, such as carbon dioxide or fluorocarbon gases, compressed to sufficient pressure to least partially liquefy the gas within the cavity 48. Alternatively, fluids containing gases such as argon, nitrogen, helium argon, or other combinations thereof that remain in gaseous form may be stored within the cavity 48. As described elsewhere herein, the pressurized fluid contained within the cavity 48 may be used to generate the forces to operate the device 6, e.g., to inject one or more agents from the syringe 70 into a subject's body.

In one example, the body 42 and cap 44 may be formed from stainless steel or other desired or suitable metal, plastic, or composite material, e.g., formed by one or more of drawing, stamping, machining, casting, molding, and the like. For example, the body 42 may be deep drawn from sheet metal, e.g., a round sheet metal blank of Type 305 stainless steel, using one or more dies and punches (not shown), to form a main barrel region, the enclosed end 42*a*, an optional tapered shoulder region, and the outlet end 42*b* defining an opening to which the cap 44 is attached.

In the example shown in FIGS. 4A-4C, the closure 46 may be a ball or other member that may be biased or otherwise configured to close an outlet in the cap 44 yet may be directed away from the cap 44, e.g., into the canister 40, by the opener mechanism 60 to open the outlet and release the pressurized gas within the cavity 48. In this example, the opener mechanism 60 includes an opener pin 62 extending through the proximal hub 14*a* of the drive assembly 12 including a proximal or first end 62*a* disposed adjacent the enclosed proximal wall 8*c* of the housing 8, and a distal end 64 disposed adjacent the cap 44, e.g., including a tapered tip 64*a* sized to enter the outlet and push the closure 46 away from the outlet. For example, the proximal end 62*a* of the opener pin 62 may abut the proximal end 8*c* of the housing 8 to prevent proximal movement of the opener pin 62, e.g., when the drive assembly 12 is directed proximally. Consequently, when the drive assembly 12 is initially directed proximally, the canister 40 may be directed proximally to cause the tip 64*a* of the opener pin 62 to enter the outlet and push the closure 46 into the outlet end 42*b* away from the cap 44 to release the pressurized gas, as described further elsewhere herein.

Optionally, as shown in FIG. 4C, the opener pin 62 may include one or more features configured to prevent the opener pin 62 from moving away from the gas canister 40 after the outlet is opened. For example, a plurality of ratchets or detents 66 may be provided on one or both of the opener pin 62 and the proximal hub 14*a* of the drive assembly 12 that allow the drive assembly 12 to move proximally relative to the opener pin 62 with minimal interference. However, after the drive assembly 12 has retracted to cause the opener pin 62 to open the outlet, the detents 66 couple the opener pin 62 to the drive assembly 12 or otherwise limit movement such that the opener pin 62 follows subsequent distal movement of the drive assembly 12 to prevent the outlet from closing, e.g., if the drive assembly 12 and canister 40 were to otherwise move distally away from the opener pin 62.

Alternatively, the cap 44 may be an enclosed cap including a septum or other weakened region (not shown) that may be opened by the opener mechanism. In this alternative, the opener mechanism may include a puncture pin (not shown) configured to puncture or preferentially tear the septum. Additional information regarding canisters that may be used and methods for making them may be found in U.S. Publication No. 2017/0258583, the entire disclosure of which is expressly incorporated by reference herein.

As shown in FIGS. 4A-4C, the canister 40 may be oriented with the outlet end 42*b* proximal to the enclosed end 42*a*, and the opener mechanism 60 may be provided proximal to the outlet end 44. Alternatively, the orientation may be reversed with the outlet end 42*b* oriented distally and the opener mechanism 60 provided distal to the outlet end 42*b* (not shown). In this alternative, the opener mechanism may be coupled to the drive assembly 12 and the canister 40 may be substantially stationary within the housing 8 such that proximal movement of the drive assembly 12 directs the opener pin proximally to open the canister.

Returning to FIG. 1B, the drive assembly 12 includes a pair of proximal seals 32 sealing the proximal chamber 30, e.g., a first or proximal O-ring 32*a* mounted around the proximal hub 14*a* and a second or distal O-ring 32*b* mounted around the first region 22*a* of the annular wall, e.g., in respective annular grooves or recesses. The O-rings 32*a*, 32*b* may slidably engage the inner wall 10*a* of the housing 8 to provide a fluid-tight seal sealing the proximal chamber 30 while accommodating axial movement of the drive assembly 12 within the housing 8. For example, as described further elsewhere herein, when the pressurized gas is released from the canister 40, the pressurized gas passes through the first chamber 22 and the passages 28 into the proximal chamber 30 to generate a distal force that advances the drive assembly 12 distally to direct the needle 78 out the distal end 8*b* of the housing 8 into the subject's skin.

To achieve the distal force, the second O-ring 32*b* may have a larger outer diameter than the first O-ring 32*a* and the inner wall 10*a* of the housing 8 may include first and second regions corresponding to the diameters of the O-rings 32*a*, 32*b*. For example, as best seen in FIGS. 4A, 4B and 5C, the inner wall 10*a* may include a first or proximal region 10*a*1 extending distally from the first O-ring 32*a* and a second or distal region 10*a*2 extending distally from the second O-ring 32*b* that has a larger diameter than the first region 10*al*. The first O-ring 32*a* slidably engages the first region 10*a*1 and the second O-ring 32*b* slidably engages the second region 10*a*2 when the drive assembly 12 moves distally from its initial position when the device 6 is activated.

The O-rings 32*a*, 32*b* and proximal chamber 30 are configured to advance the drive assembly 12 distally, i.e., to direct the needle 78 out of the housing 8 into a subject's skin, as described further elsewhere herein. When the pressurized gas enters the proximal chamber 30 (immediately after being released from the canister 40), the pressure generates a net-distal force to direct the drive assembly 12 distally due to the difference in diameters of the O-rings 32*a*, 32*b*. Given the difference in diameters, i.e., with the second or distal O-ring 32*b* having a larger diameter than the first or proximal O-ring 32*a*, the surface area of the second O-ring 32*b* exposed to the gas pressure is also larger than the first O-ring 32*a*. Given the uniform pressure from the pressurized gases acting on the opposing surface areas, the distal force acting on the second O-ring 32*b* is greater than the proximal force acting on the first O-ring 32*a*, thereby generating the net-distal force that causes the drive assembly 12 to advance distally.

Returning to FIGS. 1A and 1B, the syringe 70 generally includes a barrel 72 including a closed distal end 72*a* from which the needle 78 extends and an open proximal end 72*b* that slidably receives a piston or stopper 74 to enclose an agent chamber 73 that contains one or more therapeutic and/or diagnostic agents, e.g., in liquid or other flowable form. The proximal end 72*b* and the distal end 16 of the drive assembly 12 may include including cooperating features to secure the syringe 70 to the drive assembly 12, e.g., to couple axial movement together. For example, as best seen in FIG. 1B, the proximal end 72*b* of the barrel 72 may include one or more flanges, e.g., a radial flange or a pair of opposing flanges 76, that may be received within a corresponding recess in the distal end 16 of the drive assembly 12. In addition or alternatively, one or more detents, ridges, or other features (not shown) may be provided on the drive assembly 12 for securing the syringe 70.

In one example, the syringe 70 may be a pre-filled syringe, e.g., formed from glass, plastic, and the like, filled with a predetermined volume of agent, e.g., corresponding to a single dose for a patient. Alternatively, the agent chamber and needle may be integrated into the drive assembly if desired (not shown). In a further alternative, the syringe 70 (or integral agent chamber) may include a distal port (not shown) without a needle, such that a separate needle (also not shown) may be coupled to the port, e.g., using a Luer fitting, mating threads, and/or other cooperating connectors, immediately before an injection or otherwise as desired.

The plunger 50 may be an elongate rod or other member including a proximal end 52 that is slidably disposed within the second chamber 26, e.g., initially immediately adjacent the first chamber 20, and a distal end 54 coupled to the stopper 74. The plunger 50 is movable from an initial or retracted position (e.g., shown in FIGS. 1B, 5A, and 5B) to a final or extended position (e.g., shown in FIG. 7A), e.g., wherein the distal end 54 extends from the second end 16 of the drive assembly 12 into the agent chamber 73 of the syringe 70.

A flange or other guide member 53 is provided on the proximal end 52 of the plunger 50 that slidably engages a wall of the second chamber 26. Consequently, when pressurized gas enters the second chamber 26 (via the first chamber 22), the pressure generates a distal force to direct the plunger 50 distally from the initial position towards the final position to advance the stopper 74 and deliver the one or more agents from the agent chamber 73 through the needle 78 into the subject, as described further elsewhere herein.

Optionally, a syringe spacer or adapter 75 may be provided that may provide an interface between the distal end 54 of the plunger 50 and the piston 74, e.g., to provide connectors therebetween and/or ensure proper spacing such that the piston 74 is advanced in conjunction with the plunger 50. Thus, different length spacers 75 may be provided to allow different length syringes to be loaded into the housing 8 while properly positioning the needle 78 adjacent the distal end 8*b* of the housing 8. For example, during manufacturing or assembly, a syringe 70 may be selected that may be inserted into the housing 8, e.g., through the opening in the distal end 8*b* and coupled to the distal end 16 of the drive assembly 12. Before loading the syringe 70, a corresponding spacer 74 may be coupled to the piston 74 or distal end 54 of the plunger 50.

Optionally, the drive assembly 12 may include a wall or intermediate passage (not shown) between the first and second chambers 22, 26. The intermediate passage may have a relatively small diameter to provide a restrictor to reduce pressure rise time within the second chamber 26, e.g., to enhance initial flow of the pressurized gas into the proximal chamber 30 to advance the drive assembly 12 and needle 78 before the plunger 50 begins to advance. Alternatively, a precision orifice (not shown) may be inserted between the first and second chambers 22, 26, if desired to act as a restrictor. For example, an orifice may i) slow down the transient flow of gas, slowing the rise of pressure imparted to the plunger 50, e.g., providing a soft-start to the injection, reducing/eliminating pressure shock waves in the fluid to be injected in the syringe and possibly reducing patient pain as the drug injection is gently initiated; and/or ii) slow down the steady state flow of gas, reducing the otherwise pressure imparted to the plunger 50, providing a limiting effect to the flow rate of the drug injected into the patient.

Figure 6B:
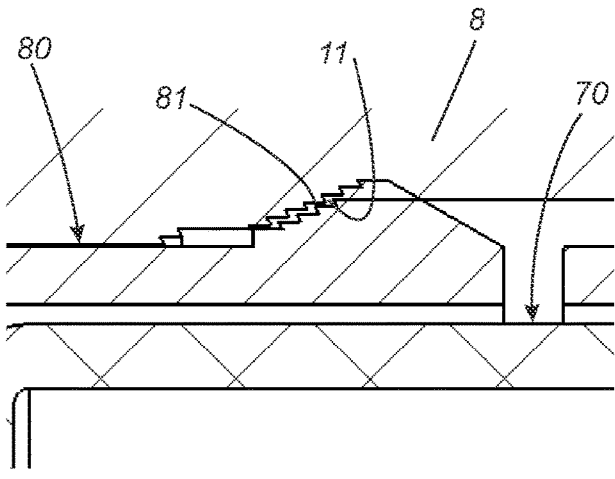
FIG. 6B is a detail showing exemplary features on the activation cap and outer housing that engage when the drive assembly advances to prevent distal movement of the activation cap during advancement of the drive assembly.
Figure 6C:
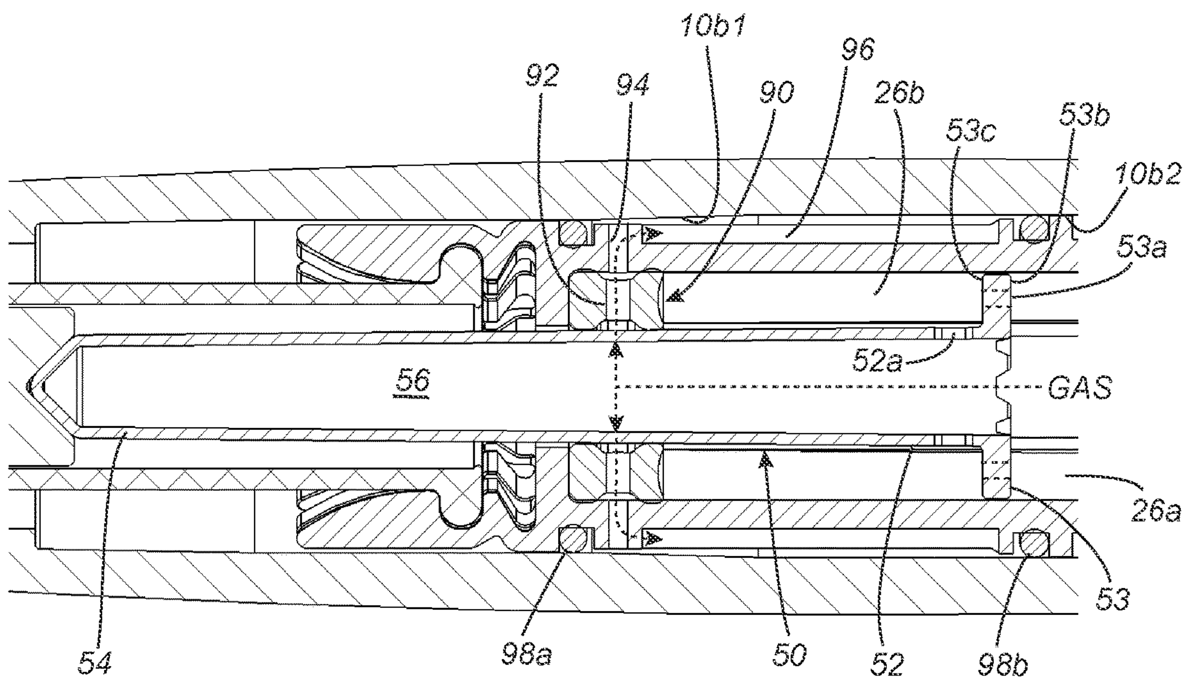
FIG. 6C shows an example of a plunger that may be included within the drive assembly that includes a plunger distal end that is smaller than a plunger proximal end.

Optionally, as shown in FIG. 6C, the flange 53 on the proximal end of the plunger 50 may include one or more passages 53*a* that extend between proximal and distal surfaces 53*b*, 53*c* of the flange 53. For example, the flange 53 may include a plurality of circular or other enclosed passages 53*a* spaced apart from one another around a circumference of the flange 53, each extending between the proximal and distal surfaces 53*b*, 53*c*. Alternatively, the passage (s) may be grooves formed in the outer surface of the flange (not shown) that extend between the proximal and distal surfaces 53*b*, 53*c*.

In this option, the flange 53 may be sized and/or shaped to slidably engage a wall of the second chamber 26, e.g., to allow the plunger 50 to move from the initial to the extended position, but does not require O-rings or other seals. For example, the flange 53 may be a cylindrical head having a larger outer diameter than the plunger 50 that is integrally molded or otherwise formed with the plunger 50, or that is manufactured separately and permanently attached to the plunger 50.

The optional passage(s) communicate between a region 26*a* of the second chamber 26 proximal to the flange 53 and a region 26*b* distal to the second chamber 26 surrounding plunger 50. A cylinder seal 90 may be provided within the drive assembly 12, e.g., at the distal end of the second chamber 26 that may slidably engage the plunger 50, i.e., to provide a fluid-tight seal with an inner wall of the second chamber 26 without interfering substantially with axial movement of the plunger 50. The seal 90 may include one or more passages 92, e.g., extending radially outwardly from an inner surface of the seal 90, which may communicate, in turn, with one or more passages 94 in the wall of the drive assembly 12 to deliver pressurized gas into a distal chamber 96, as described further elsewhere herein.

Optionally, the plunger 50 may also include a plunger chamber 56, e.g., extending from an open proximal end 52 of the plunger 50 to a closed distal end 54, e.g., as best seen in FIG. 6C. Consequently, when pressurized gas enters the second chamber 26, the gas may pass freely through the passage(s) 53*a* into both sides of the second chamber 26 around the plunger 50 and into the plunger chamber 56, as described further below.

For example, when the canister 40 is opened to release the pressurized has, the initial volume that the gas must fill (including the first chamber 22 around the canister 40, the proximal chamber 30, the second chamber 26 around the plunger 50 and, optionally, the plunger chamber 56) may result in an initial pressure drop as the gas fills the available volume. However, as the plunger 50 advances, the change in volume that the gas must fill increases only minimally (e.g., the volume the plunger 50 occupies within the second chamber 26 that is displaced out of the distal end 16 of drive assembly 12). Consequently, because the volume change is minimized, the resulting force applied by the pressure on the plunger 50 may remain substantially constant or reduce only slightly. Thus, the resulting force drop applied to the plunger 50 may be minimized, which may provide a more uniform delivery rate of the agent from the syringe 70. Additional information regarding plungers that may provide reduced pressure drop can be found in co-pending U.S. application Ser. No. 17/965,707, the entire disclosure of which is expressly incorporated by reference herein.

Optionally, as shown in FIG. 6C, the proximal end 52 of the plunger 50 may have a larger diameter or other cross-section than the distal end 54 of the plunger 50. For example, as shown, the outer diameter or cross-section may taper between the proximal and distal ends 52, 54 of the plunger 50. Such a tapered shape may increase the cross-sectional area of the plunger 50 as it advances from the initial position towards the final position, which may minimize the change in the distal force applied to the syringe stopper due to volume change, which may be particularly useful for applications where consistent rates of delivery are desired.

It will be appreciated that any of these optional features related to the plunger 50 may be combined together or omitted, as desired.

Figures 7A, 7B, 7C:
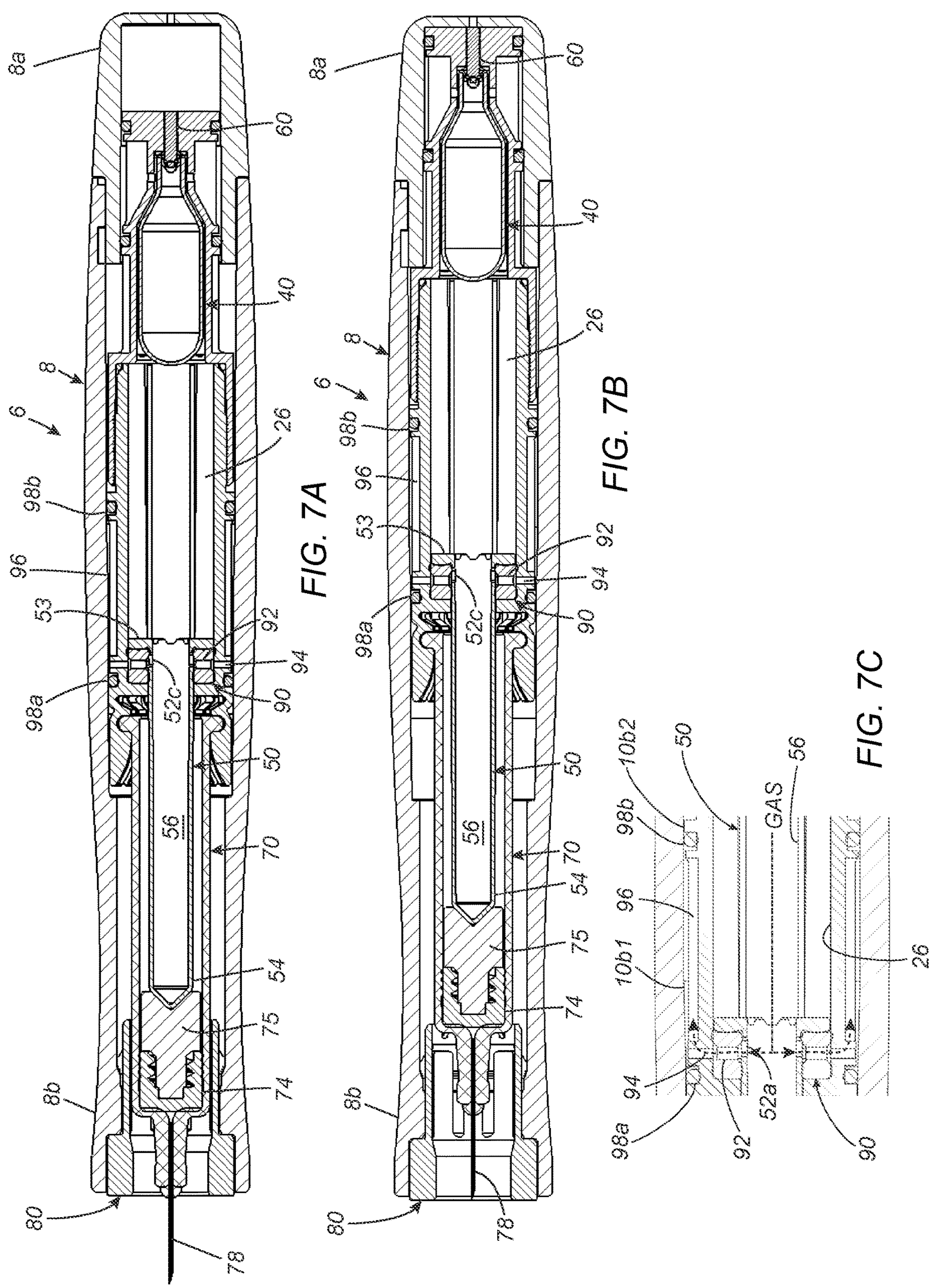
FIGS. 7A and 7B are cross-sections of the device of FIG. 6A showing the plunger fully advanced distally to open a fluid path to a distal chamber sealed by O-rings, thereby causing the drive housing to retract proximally to withdraw the needle back into the housing.
FIG. 7C is a detail showing an exemplary flow path that delivers pressurizing gas into the distal chamber.

Returning to FIG. 1B with additional reference to FIGS. 6C and 7C, the drive assembly 12 includes a pair of distal seals 98 sealing the distal chamber 96, e.g., a first or distal O-ring 98*a* and a second or proximal O-ring 98*b* mounted around the second portion 24 of the drive assembly 12, e.g., in respective annular grooves or recesses. The O-rings 98*a*, 98*b* may slidably engage the inner wall 10*b* of the housing 8 to provide a fluid-tight seal sealing the distal chamber 96 while accommodating axial movement of the drive assembly 12 within the housing 8. The distal seals 98 and distal chamber 96 may be configured such that, when the plunger 50 reaches the final position (after injecting the agent(s) into the subject), pressurized gas enters the distal chamber 96 and generates a proximal force to retract the drive assembly 12 proximally to direct the needle 78 back into the distal end 8*b* of the housing 8, e.g., as shown in FIGS. 7A and 7B.

For example, the proximal end 52 of the plunger 50 includes one or more passages 52*a*, e.g., extending radially outward from the proximal end 52 distal to the flange 53. When the plunger advances to the final position, e.g., as shown in FIGS. 7A-7C, the passage(s) 52*a* become aligned with the passages 92 in the cylinder seal 90. The pressurized gas within the second chamber 26 (released from the canister 40 to advance the plunger 50) is then free to travel from the plunger chamber 56 through the passages 52*a*, 92, 94 into the distal chamber 96 to generate a proximal force that retract the drive assembly 12 proximally to direct the needle 78 back into the distal end 8*b* of the housing 8.

To achieve the proximal force, the second O-ring 98*b* may have a larger outer diameter than the first O-ring 98*a* and the inner wall 10*b* of the housing 8 may include first and second regions corresponding to the diameters of the O-rings 98*a*, 98*b*. For example, as best seen in FIGS. 6C and 7C, the inner wall 10*b* may include a first or distal region 10*b*1 extending proximally from the first O-ring 98*a* and a second or proximal region 10*b*2 extending proximally from the second O-ring 98*b* that has a larger diameter than the first region 10*b*1. The first O-ring 98*a* slidably engages the first region 10*b*1 and the second O-ring 98*b* slidably engages the second region 10*b*2 when the drive assembly 12 moves proximally from its advanced position after delivery of the agent(s) within the syringe 70.

As with the O-rings 32*a*, 32*b* and proximal chamber 30, the distal O-rings 98*a*, 98*b* and distal chamber 96 are configured such that the pressurized gas generates a proximal force to retract the drive assembly 12 proximally when the pressurized gas enters the distal chamber 30, since the pressure generates a net-proximal force to direct the drive assembly 12 proximally due to the difference in diameters of the O-rings 98*a*, 98*b*. Given the difference in diameters, i.e., with the proximal O-ring 98*b* having a larger diameter than the distal O-ring 98*a*, the surface area of the second O-ring 98*b* is also larger than the first O-ring 98*a*. Given the uniform pressure from the pressurized gases acting on the opposing surface areas, the proximal force acting on the second O-ring 98*b* is greater than the distal force acting on the first O-ring 98*a*, thereby generating the net-proximal force that causes the drive assembly 12 to retract proximally.

Further, the O-rings 98*a*, 98*b* have diameters that are larger than the diameters of the proximal O-rings 32*a*, 32*b* (and the distal inner wall 10*b* has diameters that are larger than the proximal inner wall 10*a*). Consequently, the net-proximal force generated by the distal chamber 96 is greater than the net-distal force generated by the proximal chamber 30 such that the net-net force is proximal to ensure the drive assembly 12 is retracted.

It will be appreciated that the relative diameters of the proximal pair of seals 30 and the distal pair of seals 96 may be selected to generate a desired net-distal force and net-proximal force during the corresponding phases of operation of the device 6. For example, the net-distal force to initial advance the drive assembly 12 may be selected to advance the needle 78 into a subject's skin at a desired speed, e.g., a relatively low force to minimize discomfort, while the net-proximal force may be much greater, e.g., to rapidly remove the needle after delivering the agent(s) within the syringe 70. Further, the force applied to the plunger 50 to advance the plunger 50 and stopper 74 to deliver the agent(s) may be relatively high to rapidly deliver the agent(s) to minimize the overall time required to complete the injection.

The seals 32, 98, as well as other seals of the device 6, e.g., cylinder seal 90 may create a hermetically sealed or contained system in which the pressurized gas from the canister 40 is delivered into the set of chambers with minimal leakage.

Figure 2:
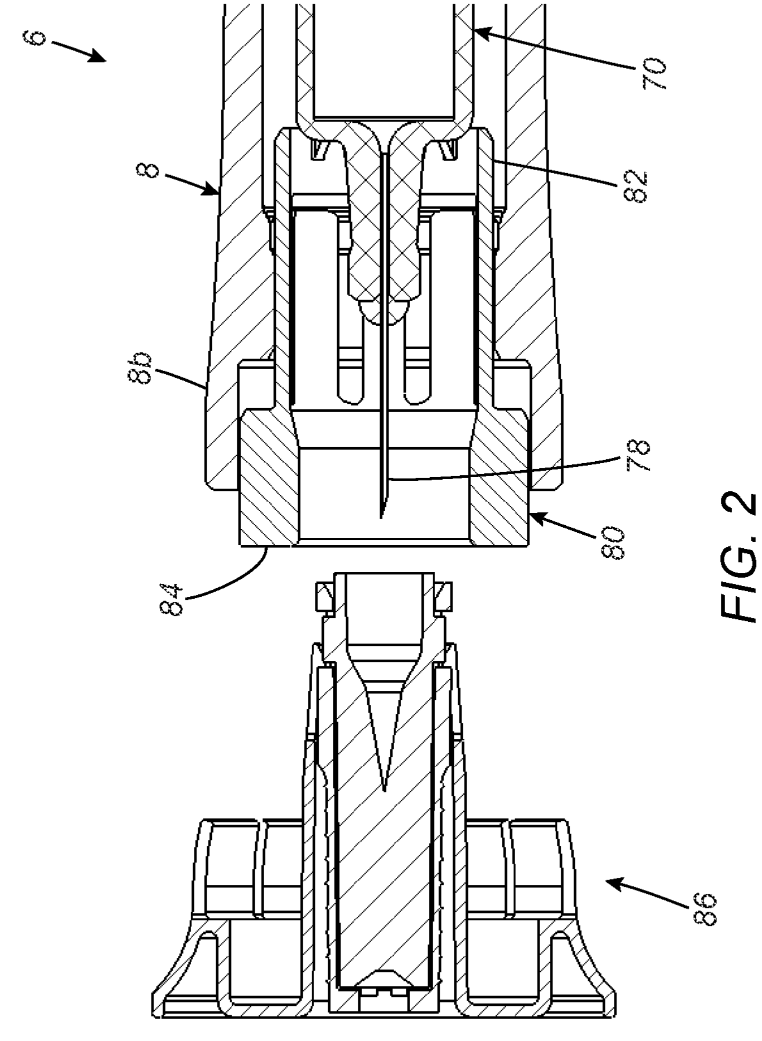
FIG. 2 is a detail of the device of FIGS. 1A and 1B with a safety cap being removed from a distal end of the housing before use.

During use, the device 6 may be provided initially with a safety cap 86 attached to the distal end 8*b* of the housing 8, e.g., as shown in FIGS. 1A and 1B. For example, the safety cap 86 may prevent the activation cap 80 from being directed proximally, e.g., by preventing the activation cap 80 from being contacted. In addition or alternatively, the safety cap 86 may include features that engage the needle shield 79 such that, when the safety cap 86 is removed, the needle shield 79 is also removed. The safety cap 86 and needle shield 79 may prevent the needle 78 from being exposed from the housing 8 prior to use. Thus, immediately before performing an injection, the safety cap 86 may be removed, e.g., as shown in FIG. 2, to expose a contact surface 84 of the activation cap 80.

Figures 3A, 3B:
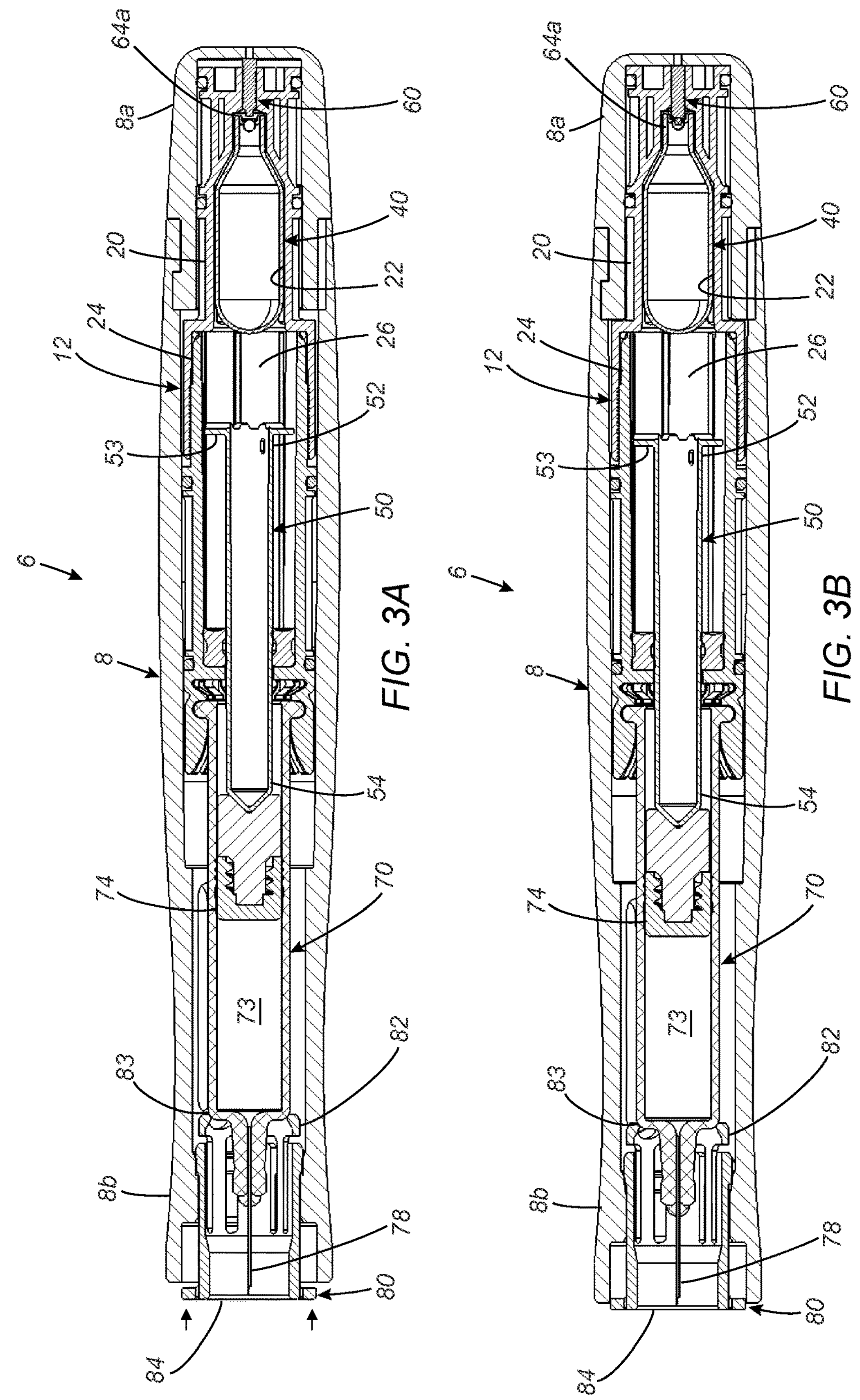
FIGS. 3A and 3B are cross-sectional views of the device of FIGS. 1A and 1B showing initial activation of the device when an activation cap is pressed against a subject's skin to direct the drive assembly proximally to release gas from a gas canister within the drive assembly.

Turning to FIGS. 3A and 3B, the contact surface 84 may be placed against a subject's skin (not shown) and then the device 6 may be pressed against the skin, thereby causing the activation cap 80 to move proximally to direct the drive assembly 12 proximally within the housing 8 to cause the opener pin 60 to open the outlet of the gas canister 40 to release pressurized gas into the first chamber 22. For example, as shown, the proximal end 82 of the activation cap 80 may include one or more detents or tabs 83 that contact the barrel 72 of the syringe 70 to push the syringe 70, thereby directing the entire drive assembly 12 coupled to the syringe 70 (including the canister 40 carried by the drive assembly 12) proximally. As the drive assembly 12 and canister 40 move proximally, the opener pin 60 opens the outlet of the canister 40 to release the pressurized gas into the first chamber 22 around the canister 40, e.g., as shown in FIG. 4C.

Figure 5A:
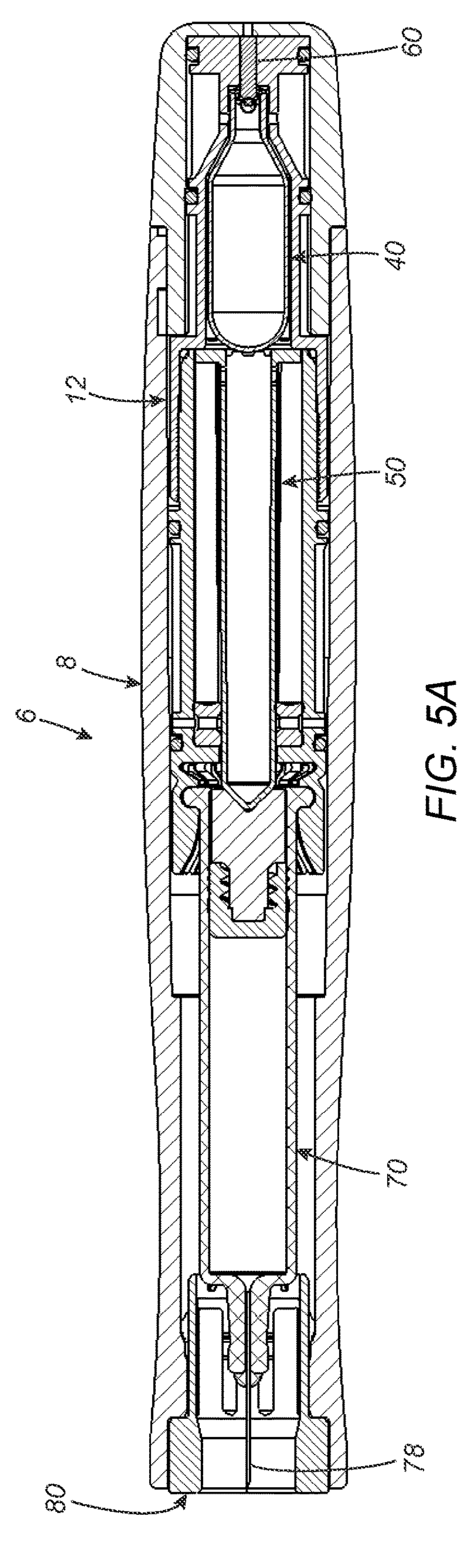
FIGS. 5A and 5B show the device of FIGS. 3A and 3B as pressurized gas causes advancement of the drive assembly distally to direct a needle of the syringe from the distal end of the housing.
Figure 5B:
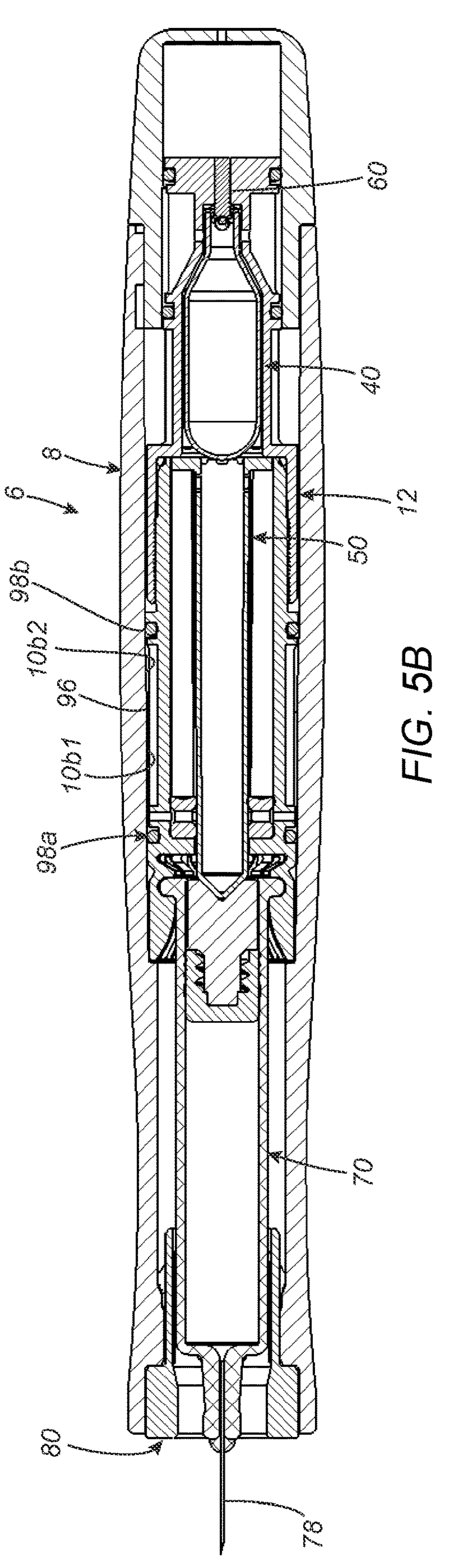
Figures 5C, 6A:
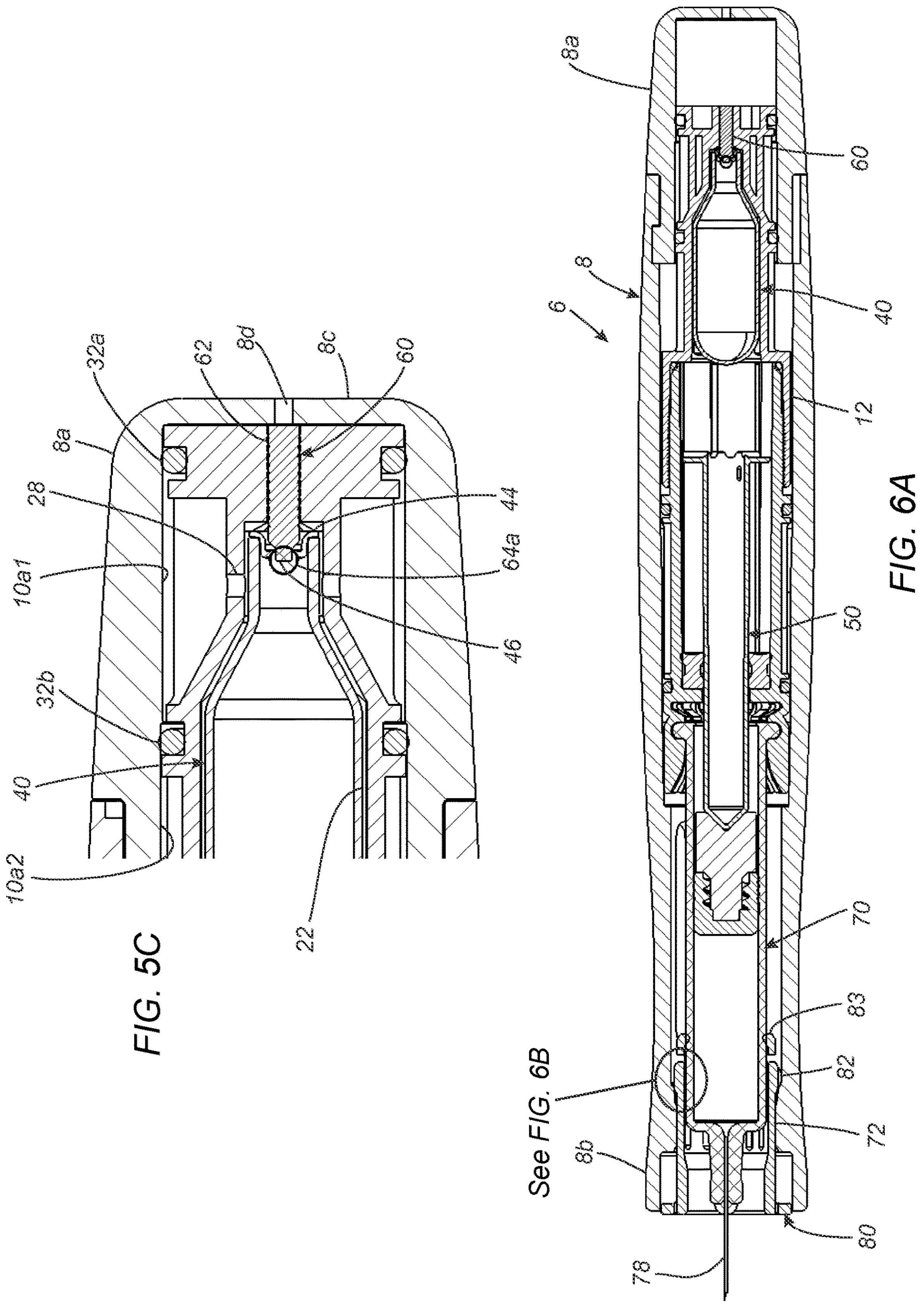
FIG. 5C is a detail showing a path pressurized gas travels into a proximal chamber sealed by O-rings that generate a distal force to advance the drive assembly.
FIG. 6A is a cross-section of the device of FIGS. 5A and 5B, showing pressurized gas from the gas canister advancing a plunger within the drive assembly to deliver one or more agents from the syringe.

As shown in FIG. 5C, the pressurized gas then enters the proximal chamber 30 sealed by the proximal seals 32 via the one or more passages 28, consequently generating a distal force to advance the entire drive assembly 12 distally to direct the needle 78 out the distal end 8*b* of the housing 8 into the subject's skin, e.g., as shown in FIGS. 5A and 5B. If the canister 40 includes a ball closure 46, e.g., as shown in FIG. 5C, the features 66 may engage to cause the opener pin 60 to move distally with the drive assembly, as shown in FIG. 5B, thereby preventing the ball from closing the outlet.

As the drive assembly 12 advances, the tab(s) 83 on the activation cap 80 may be configured to deflect out of the way or otherwise allow the syringe 70 to advance into the proximal end 82 of the activation cap 80, e.g., as shown in FIG. 6A, to avoid interference with directing the needle 78 out the distal end 8*b* of the housing 8 into the subject's skin. The activation cap 80 and/or housing 8 may include one or more cooperating features to prevent the activation cap 80 from moving distally, e.g., as the drive assembly 12 and syringe 70 are advanced. For example, as shown in FIG. 6B, one or more teeth or ratchets 81, 11 may be provided on the activation cap 80 and an inner surface of the housing 8 that allow the activation cap 80 to move proximally (e.g., during initial activation) but prevent subsequent distal movement.

For example, pressing the activation cap 80 against the subject's skin may generate a relatively low force sufficient to allow the detents 83 to push the syringe 70 and drive assembly 12 proximally during initial activation, with the teeth or ratchets 81, 11 allowing such proximal motion without interference. However, once the pressurized gas is released to advance the drive assembly, a relatively greater force may be generated to deflect the detents 83 on the activation cap 80 with the teeth or ratchets 81, 11 preventing the activation cap 80 from moving distally or otherwise interfering with advancing the syringe 70 to direct the needle 78 into the subject's skin.

In addition, as shown in FIGS. 6A and 7A, the pressurized gas enters the second chamber 26 from the first chamber 22 to direct the plunger 50 distally from the initial position towards a final position to deliver the one or more agents from the syringe 70 through the needle 78 into the subject.

As shown in FIGS. 7A and 7B, when the plunger 50 reaches the final position, the pressurized gas enters the distal chamber 96 sealed by the distal seals 98, i.e., through the passages 52*a*, 92, 94, such that the pressurized gas generates a proximal force to retract the drive assembly 12 proximally to direct the needle 78 back into the distal end 8*b* of the housing 8. Thus, the entire operation of the device 6 may be triggered simply by pressing the activation cap 80 against the subject's skin with the pressurized gas communicating with the chambers to advance the needle, inject the agent(s), and retract the needle without further action from the operator. The device 6 may then be safely discarded without risk of subsequent contact with the needle 78. Optionally, the safety cap 86 and/or needle shield 79 may be reattached to the distal 8*b* of the housing 8, if desired.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for delivering one or more agents into a subject's body, comprising:

an outer housing comprising a proximal end and a distal end;

an activation cap mounted on the distal end of the housing such that a contact surface is disposed distal to the distal end of the housing;

a drive assembly slidable within the housing comprising a proximal portion adjacent the proximal end of the housing including a first chamber therein, a distal portion including a second chamber, and defining a proximal chamber between the proximal portion and the housing communicating with the first chamber;

a syringe on a distal end of the drive assembly such that a needle of the syringe is disposed adjacent the activation cap within the distal end of the housing;

a gas canister within the first chamber;

a plunger comprising a proximal end within the second chamber of the drive assembly and a distal end coupled to a piston of the syringe; and an opener pin adjacent an outlet of the gas canister;

the activation cap movable related to the housing such that, when the contact surface of the activation cap is pressed against a subject's skin, the activation cap is configured to move proximally to direct the drive assembly proximally within the housing to cause the opener pin to open the outlet of the gas canister to release pressurized gas into the first chamber and the proximal chamber; and the drive assembly comprising a pair of proximal seals sealing the proximal chamber, the proximal seals configured such that, when the pressurized gas is released from the gas canister and enters the proximal chamber, the pressurized gas generates a distal force to advance the drive assembly distally to direct the needle out the distal end of the housing into the subject's skin and the pressurized gas enters the second chamber from the first chamber proximal to the proximal end of the plunger to direct the plunger distally from an initial position towards a final position to deliver the one or more agents from the syringe through the needle into the subject.

2. The device of claim 1, wherein the drive assembly comprises a pair of distal seals sealing a distal chamber and a passage that communicates with the second chamber when the plunger reaches the final position, the distal seals configured such that, when the pressurized gas enters the distal chamber, the pressurized gas generates a proximal force to retract the drive assembly proximally to direct the needle back into the distal end of the housing.

3. The device of claim 2, wherein the distal seals comprise third and fourth O-rings slidably engaging the inner wall of the housing within a distal region of the housing such that the inner wall encloses the distal chamber.

4. The device of claim 3, wherein the third O-ring is located proximal to the fourth O-ring and the third O-ring has a larger diameter than the fourth O-ring such that the pressurized gas within distal chamber generates a net-proximal force to retract the drive assembly proximally.

5. The device of claim 4, wherein the third O-ring slidably engages a third region of the inner wall and the fourth O-ring slidably engages a fourth region of the inner wall, the third region having a larger diameter than the fourth region.

6. The device of claim 4, wherein the third and fourth O-rings have diameters than are larger than the diameter of the second O-ring such that the net-proximal force is greater than the net-distal force.

7. The device of claim 4, wherein the third and fourth O-rings have cross-sectional areas than are larger than cross-sectional areas of the second O-ring such that the net-proximal force is greater than the net-distal force.

8. The device of claim 1, wherein the proximal seals comprise first and second O-rings slidably engaging an inner wall of the housing within a proximal region of the housing such that the inner wall encloses the proximal chamber.

9. The device of claim 8, wherein the second O-ring is located distal to the first O-ring and the second O-ring has a larger diameter than the first O-ring such that the pressurized gas within proximal chamber generates a net-distal force to direct the drive assembly distally.

10. The device of claim 9, wherein the first O-ring slidably engages a first region of the inner wall and the second O-ring slidably engages a second region of the inner wall, the second region having a larger diameter than the first region.

11. The device of claim 1, further comprising a safety cap connected to the distal end of the housing distal to the activation cap to prevent the activation cap from being directed proximally.

12. The device of claim 1, further comprising a safety cap removably connected to the distal end of the housing distal to the activation cap to prevent the needle from being exposed from the housing before the safety cap is removed.

13. The device of claim 1, wherein the gas canister comprises a ball sealing the outlet that is initially spaced away from the opener pin and, wherein, as the drive assembly initially retracts, the gas canister is displaced to cause the opener pin to push the ball to open the outlet and release the gas within the gas canister.

14. The device of claim 13, wherein the open pin comprises one or more features configured to prevent the opener pin from moving away from the gas canister after the outlet is opened.

15. The device of claim 14, wherein the one or more features comprise a plurality of ratchets or detents on one or both of the opener pin and the proximal end of the drive assembly.

16. The device of claim 1, wherein the gas canister comprises a penetrable septum initially spaced away from the opener pin and, wherein, as the drive assembly initially retracts, the gas canister is displaced to cause the opener pin to penetrate the septum and release the gas within the gas canister.

17. The drive module of claim 16, wherein the septum of the gas canister is oriented proximally within the first chamber, and the opener pin is oriented distally towards the septum.

18. The device of claim 1, wherein the plunger comprises a plunger chamber extending from an opening in the proximal end communicating with the second chamber such that pressurized gas from the gas canister entering the second chamber fills the plunger chamber.

19. The device of claim 1, wherein the proximal end of the piston comprises a flange separating the second chamber into proximal and distal regions and wherein the proximal end of the piston comprises one or more passages configured to allow gas from the gas canister entering the second chamber to pass from the proximal region into the distal region.

20. A method for delivering one or more agents into a subject's body, comprising:

providing an injection device comprising an outer housing comprising a proximal end and a distal end; an activation cap mounted on the distal end of the housing such that a contact surface is disposed distal to the distal end of the housing; a drive assembly slidable within the housing comprising a proximal portion adjacent the proximal end of the housing including a first chamber therein, a distal portion including a second chamber, and defining a proximal chamber between the proximal portion and the housing communicating with the first chamber; a syringe on a distal end of the drive assembly such that a needle of the syringe is disposed adjacent the activation cap within the distal end of the housing; a gas canister within the first chamber; a plunger comprising a proximal end within the second chamber of the drive assembly and a distal end coupled to a piston of the syringe; and an opener pin adjacent an outlet of the gas canister;

placing the contact surface against the subject's skin; and pressing the device to cause the activation cap to move proximally to direct the drive assembly proximally within the housing to cause the opener pin to open the outlet of the gas canister to release pressurized gas into the first chamber and the proximal chamber, whereupon the pressurized gas enters the proximal chamber of the drive assembly sealed by a pair of proximal seals configured such that the pressurized gas generates a distal force to advance the drive assembly distally to direct the needle out the distal end of the housing into the subject's skin;

the pressurized gas enters the second chamber from the first chamber proximal to the proximal end of the plunger to direct the plunger distally from an initial position towards a final position to deliver the one or more agents from the syringe through the needle into the subject; and when the plunger reaches the final position, the pressurized gas enters a distal chamber sealed by a pair of distal seals such that the pressurized gas generates a proximal force to retract the drive assembly proximally to direct the needle back into the distal end of the housing.

21. The method of claim 20, wherein the drive assembly comprises a passage that communicates between the second chamber and the distal chamber such that, when the pressurized gas enters the distal chamber, the pressurized gas generates the proximal force to automatically retract the drive assembly proximally to direct the needle back into the distal end of the housing.

* * * * *